(12) United States Patent
Sivak et al.

(10) Patent No.: US 9,862,312 B2
(45) Date of Patent: Jan. 9, 2018

(54) UNIVERSAL MOTION SICKNESS COUNTERMEASURE SYSTEM

(71) Applicant: THE REGENTS OF THE UNIVERSITY OF MICHIGAN, Ann Arbor, MI (US)

(72) Inventors: Michael Sivak, Ann Arbor, MI (US); Brandon Schoettle, Ypsilanti, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 15/478,275

(22) Filed: Apr. 4, 2017

(65) Prior Publication Data
US 2017/0291538 A1    Oct. 12, 2017

Related U.S. Application Data

(60) Provisional application No. 62/318,903, filed on Apr. 6, 2016, provisional application No. 62/317,979, filed on Aug. 8, 2016.

(51) Int. Cl.
*B60Q 3/80* (2017.01)
*B60Q 3/66* (2017.01)
*B60Q 3/51* (2017.01)
*B60Q 3/70* (2017.01)
*A61M 21/02* (2006.01)
*A61M 21/00* (2006.01)

(52) U.S. Cl.
CPC ............... *B60Q 3/80* (2017.02); *A61M 21/02* (2013.01); *B60Q 3/51* (2017.02); *B60Q 3/66* (2017.02); *B60Q 3/70* (2017.02); *A61M 2021/005* (2013.01); *A61M 2021/0044* (2013.01)

(58) Field of Classification Search
None
See application file for complete search history.

(56) References Cited

U.S. PATENT DOCUMENTS

| | | | |
|---|---|---|---|
| 7,357,550 B2 * | 4/2008 | Li | G02B 27/0994 257/E33.071 |
| 7,717,841 B2 | 5/2010 | Brendley et al. | |
| 2001/0000459 A1 * | 4/2001 | Kania | A61M 21/00 381/98 |
| 2004/0102676 A1 * | 5/2004 | Brendley | A61M 21/00 600/27 |
| 2010/0141905 A1 | 6/2010 | Burke | |
| 2013/0163273 A1 | 6/2013 | Ticktin | |

FOREIGN PATENT DOCUMENTS

| | | |
|---|---|---|
| JP | 2008-230575 A | 10/2008 |
| KR | 10-2015-0045164 A | 4/2015 |

OTHER PUBLICATIONS

International Search Report and Written Opinion of the International Searching Authority dated Jul. 11, 2017 regarding PCT/US2017/026205.

* cited by examiner

*Primary Examiner* — Dedei K Hammond
(74) *Attorney, Agent, or Firm* — Harness, Dickey & Pierce, P.L.C.

(57) ABSTRACT

A motion sickness countermeasure system for a user within a vehicle having a light array system configured to output visual stimuli presented in a field of view of the user; and a controller outputting a control signal to the light array system to activate the light array system in such a way as to mimic the visual input one would receive if one were to look outside the vehicle.

20 Claims, 5 Drawing Sheets

UNIVERSAL MOTION SICKNESS COUNTERMEASURE SYSTEM

CROSS-REFERENCE TO RELATED APPLICATIONS

This application claims the benefit of U.S. Provisional Application No. 62/318,903, filed on Apr. 6, 2016 and U.S. Provisional Application No. 62/371,979, filed on Aug. 8, 2016. The entire disclosures of the above applications are incorporated herein by reference.

FIELD

The present disclosure relates to motion sickness and, more particularly, relates to universal countermeasure systems for motion sickness in moving vehicles.

BACKGROUND AND SUMMARY

This section provides background information related to the present disclosure which is not necessarily prior art. This section also provides a general summary of the disclosure, and is not a comprehensive disclosure of its full scope or all of its features.

Motion sickness most often results from a sensory conflict between inputs from the visual and vestibular systems. In conventional vehicles, drivers themselves are generally not susceptible to motion sickness because, by looking at the road and controlling the vehicle, they experience no such conflict. On the other hand, a substantial proportion of passengers who attempt to perform reading and other activities, do experience motion sickness. For example, about 50% of adults get motion sick, at least occasionally, when reading a book in a moving vehicle. It is important to note that motion sickness will be of even greater concern with autonomous and self-driving vehicles, because all persons aboard will now be passengers.

It is known that having moving lights on the border of a display for on-board video viewing substantially reduces the extent of motion sickness. However, this countermeasure is display specific—it is tied to the video monitor, and it stops being effective when one looks away from the monitor. Furthermore, when performing tasks without video screens (such as reading a book), the countermeasure is not applicable.

According to the principles of the present teachings, a universal solution to motion sickness is provided as it remains constantly in the field-of-view of the person. It involves presenting, in the visual periphery, lights or similar visual stimuli that are timed in such a way that the apparent movement of the stimuli mimics (in terms of velocity, acceleration, lateral movement, vertical movement, yaw rate, roll rate, pitch rate, or any other parameter relating to motion) the visual input one would receive if one were to look outside the vehicle. In addition to the specific vehicle motion, simulation of reference points outside the vehicle, such as an artificial horizon, may also be presented with this array of stimuli.

It should be understood that the principles of the present teachings have a wide range of applicability and can be applied to any passenger compartment of a moving vehicle or device where visual perception of natural cues may be limited. These principles can be incorporated in to any one of a number of devices or interiors, such as, but not limited to, the rim of glasses, goggles, or other headgear and/or within the passenger compartment of a moving vehicle, such as in the pillars, headliner, roof, sidewalls, doors, seats, floor, dashboard, console, windows or areas traditionally used as windows, and the like.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
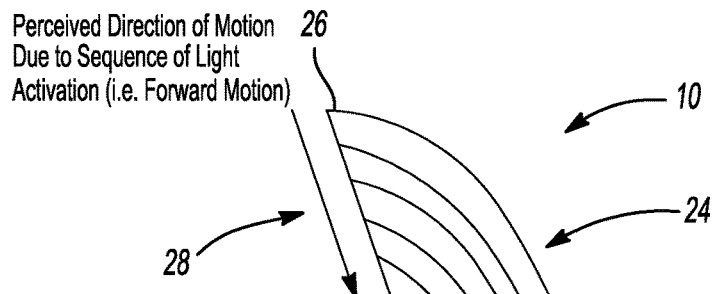
FIG. 1 illustrates a schematic view of a universal motion sickness countermeasure system according to some embodiments of the present teachings employing a sequentially activated light array presented using lightpipes.
Figure 1:
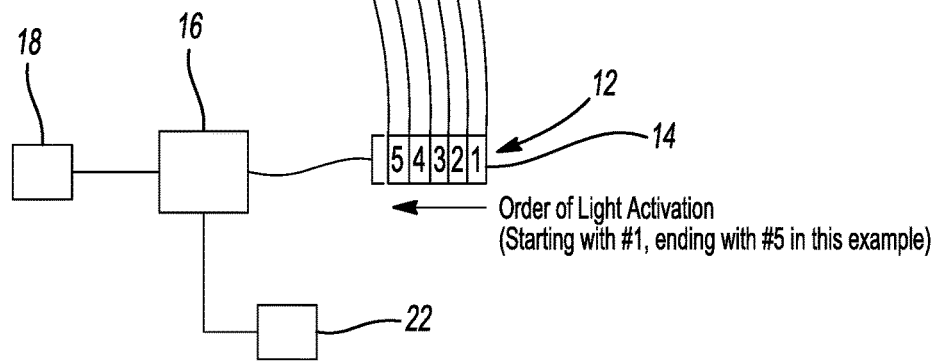

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

In some embodiments, the present teachings comprises a wearable array of lights or similar visual stimuli (such as LEDs, LCDs, or video displays, mounted on goggles, glasses, hat brims, etc.), or vehicle mounted arrays of lights or similar visual stimuli (mounted in the vehicle interior in such locations as the pillars, headliner, roof, sidewalls, doors, seats, floor, dashboard, console, windows or areas traditionally used as windows, and the like) presented in the viewer's peripheral field of view in such a way as to mimic the specific motion (such as velocity, yaw rate, and/or pitch rate) of the vehicle. Presenting such apparent motion and outside reference points in the viewer's peripheral field of view allows them to look away from the outside scene, such as would occur when working on a laptop, reading, playing video games, watching movies, etc., yet still being able to perceive the motion of the vehicle while performing such tasks. Elimination of outside visual motion stimuli, while retaining the motion stimuli within the vestibular system (i.e., the inner ear) is a main contributor to motion sickness. Conversely, retaining or simulating such visual stimuli should help reduce the frequency and severity of motion sickness, as the sensory mismatch (i.e., motion sensed in the vestibular system yet no perceived visual motion) is eliminated.

According to the principles of the present teachings, a universal motion sickness countermeasure system 10 is provided having advantageous construction and method of operation. In some embodiments, universal motion sickness countermeasure system 10 comprises a light array system 12 having one or more individual light elements 14 being controlled by a controller 16 in response to movement of a vehicle or similar system 100. It should be noted that although the present teachings will be described in connection with an automotive vehicle 100, the principles of the present teachings are not limited thereto and can be applied to other vehicle types, including aircraft, ships, boats, trains, and other transportation modes where users are susceptible to motion sickness.

Universal motion sickness countermeasure system 10 can further include a power source 18, including a vehicle provided sources and/or a battery or renewable energy source. It should be understood that the principles of the present teachings can be employed, incorporated, or otherwise used in any one of a number of configurations or vehicles. By way of non-limiting example, universal motion sickness countermeasure system 10 can be incorporated into any system that is capable of being displayed to the visual system of a user, passenger, occupant, or mammal susceptible to the effects of motion sickness. In some embodiments, universal motion sickness countermeasure system 10 can be employed as part of a wearable solution, such as part of traditional eyewear, googles, masks, pods, or headwear. Alternatively or additionally, universal motion sickness countermeasure system 10 can be employed as part of a fixed solution, such as incorporated into passenger compartment components of the vehicle (e.g. pillars, headliner, roof, sidewalls, doors, seats, floor, dashboard, console, windows or areas traditionally used as windows, and the like).

Figure 2:
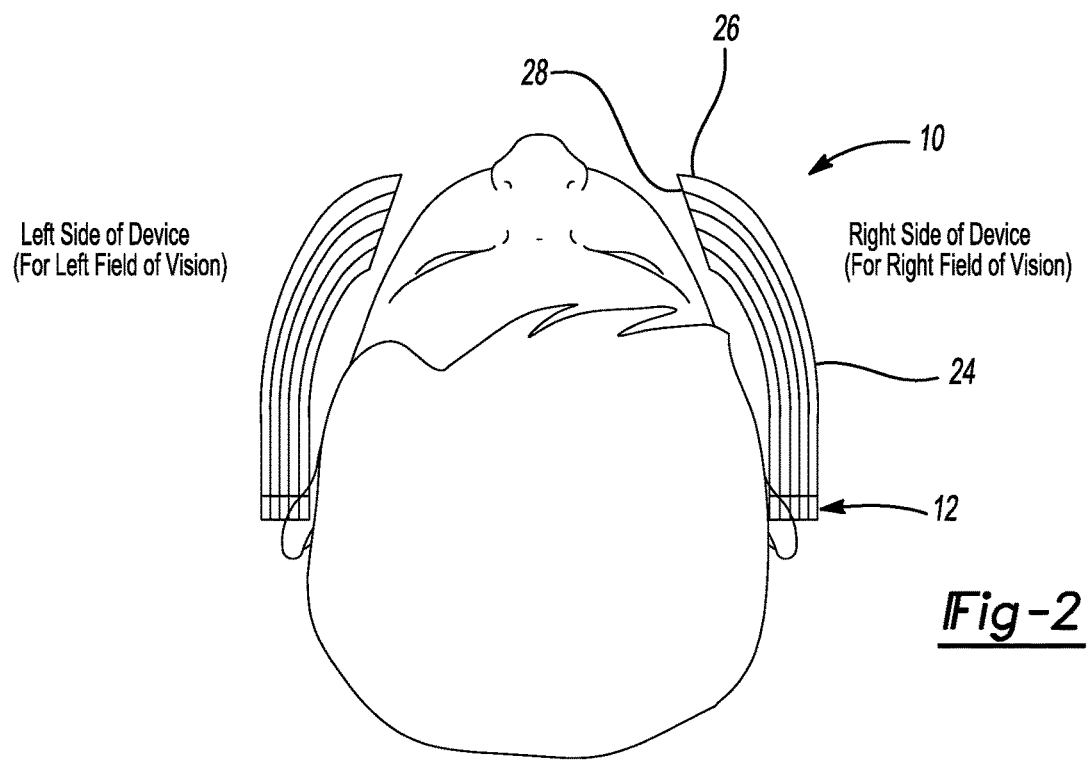
FIG. 2 illustrates a schematic view of the universal motion sickness countermeasure system of FIG. 1 being proximally located relative to a user (irrespective of any specific mounting method or method of wearing the device or system).
Figure 3:
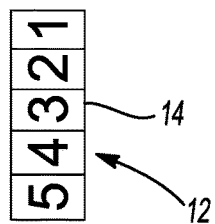
FIG. 3 illustrates a schematic view of a universal motion sickness countermeasure system according to some embodiments of the present teachings employing a sequentially activated light array.

In some embodiments, light array system 12 can comprise one or more light elements 14 disposed in a panel, a strip, an array, or other arrangement. Light elements 14 can include LEDs, LCDs, diodes, lasers, luminescence sources, or any other light outputting source. As illustrated in FIGS. 1-4, in some embodiments, light array system 12 can comprise a plurality of light elements 14 disposed in a linear pattern along a singular axis (e.g. x-axis as illustrated in FIGS. 1-2, y-axis as illustrated in FIG. 3). This arrangement is particularly well suited for use in simulating motion in a singular direction. However, in some embodiments, as illustrated in FIG. 5, light array system 12 can comprise a plurality of light elements 14 disposed in a multi-dimensional pattern defining multiple axes of orientation (e.g. both x-axis and y-axis). This arrangement is particularly well suited for use in simulating motion in multiple directions and/or yaw.

In some embodiments, controller 16 is operably coupled to each of the plurality of light elements 14 of light array system 12 to individually control activation thereof. In response to such activation, at least one of the plurality of light elements 14 outputs light energy to be viewed by the user. Through the rapid and controlled activation of the plurality of light elements 14, the resultant pattern of light output or energy viewed by the user produces a visual response in the user having a desired effect that complements the associated vestibular response experienced by the user. By producing a visual response that complements the experienced vestibular response, the stimuli from the user's visual and vestibular systems are easily reconciled by the brain, thereby avoiding the typical sensory conflict that results in motion sickness.

To this end, in some embodiments, controller 16 can be coupled to the power source 18, such as the vehicle power source or a portable or renewable power source. Controller 16 can comprise one or more sensors or transducers 22 (e.g. gyroscopes, accelerometers, and similar sensors) for measuring velocity, acceleration, lateral movement, vertical movement, yaw rate, roll rate, pitch rate, or any other parameter relating to motion. It should be understood that sensors or transducers 22 can be incorporated directly into universal motion sickness countermeasure system 10 or can be obtained from the existing systems of vehicle 100. It should also be understood that the parameters used for determining the resultant light pattern of light array system 12 can be calculated or otherwise indirectly deduced from measured and non-measured parameters, such as via mathematical computation of position, velocity, and/or acceleration or other control algorithm. In response to such, controller 16 can computationally or otherwise determine a desired resultant light pattern and output a control signal to each of the plurality of light elements 14 of light array system 12. Accordingly, each of the plurality of light elements 14 can define a unique, discrete position and/or signature to ensure proper activation and display of the resultant light pattern.

In some embodiments, such as illustrated in FIGS. 1-2, light array system 12 can comprise one or more light transfer features 24, such as light pipes, for transmitting the light energy from the corresponding light element 14 to a desired position relative to the user. In some embodiments, a plurality of light pipes 24 can be operably coupled with light elements 14 to guide light energy from light element 14 to a distal end 26 of each of the plurality of light pipes 24. As illustrated in FIG. 1, each of the plurality of light pipes 24 can define similar or different lengths such that distal end 26 can be positioned to provide the desired sensory stimulation. In particular, light array system 12 can be activated such that a first light element $14^1$ outputs light energy along light pipe $24^1$ and, similarly, additional light elements $14^n$ output light energy along light pipes $24^n$. It should be noted that n denotes an unlimited number of elements. However, for brevity of discussion, only five (5) light elements are currently illustrated. Each of the light pipes $24^1$, $24^n$ can be arranged such that distal end 26 form an inclined or angular surface 28 viewable by the user that simulates transitional movement of the vehicle 100.

In some embodiments, as illustrated in FIG. 5, light array system 12 can comprise a plurality of rows and columns of light elements 14 for displaying movement of vehicle 100. As discussed herein, light array system 12 can simulate velocity, acceleration, lateral movement, vertical movement, yaw rate, roll rate, pitch rate, or any other parameter relating to motion. For example, assuming travel of vehicle 100 to the left (in FIG. 5), light elements 14 can be sequentially activated to illuminate from left to right to simulate linear movement. The rate of and duration of illumination of light elements 14 can affect the perceived motion by the user. Moreover, light elements 14 can be sequentially activated to illuminate from top to bottom (or vice versa) to simulate acceleration and/or pitch. Still further, light elements 14 can be activated to illuminate a horizon line, which rotation of the line about an axis into the light array system 12 can simulate roll and/or yaw. Such depiction, irrespective of using a linear or multi-directional array, can produce perceived motion that is directly representative of vehicle 100 and/or the perceived corresponding vestibular motion.

Figure 4:
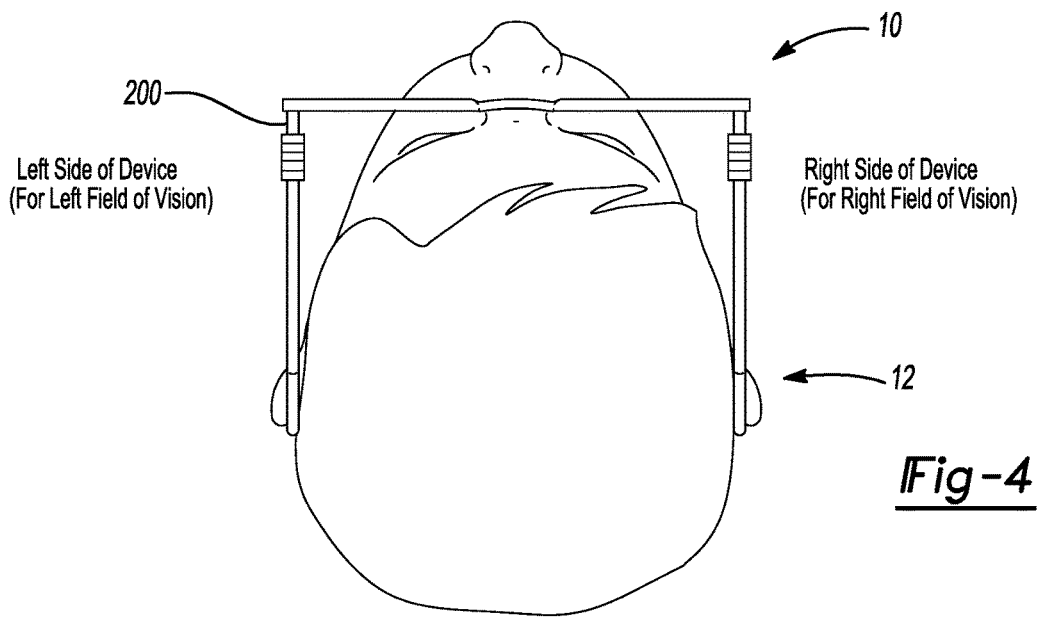
FIG. 4 illustrates a schematic view of a universal motion sickness countermeasure system according to some embodiments of the present teachings being incorporated into a wearable frame, such as glasses, goggles, or headgear.
Figure 5:
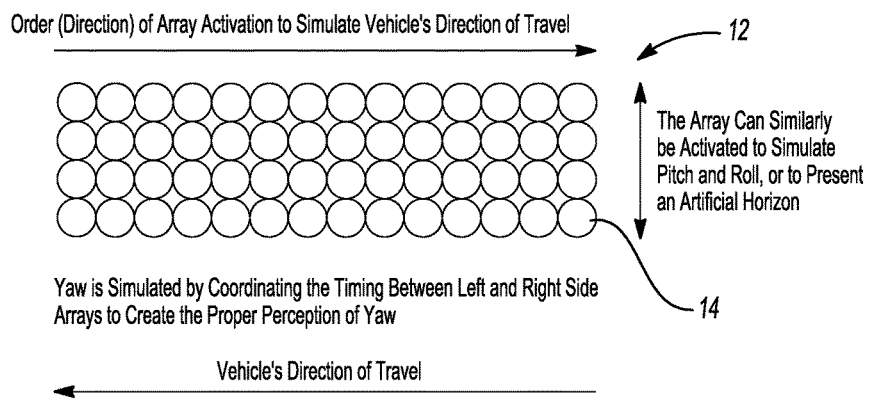
FIG. 5 illustrates an array of visual stimuli of the universal motion sickness countermeasure system and a general method for presenting such stimuli to visually simulate motion.
Figure 6:
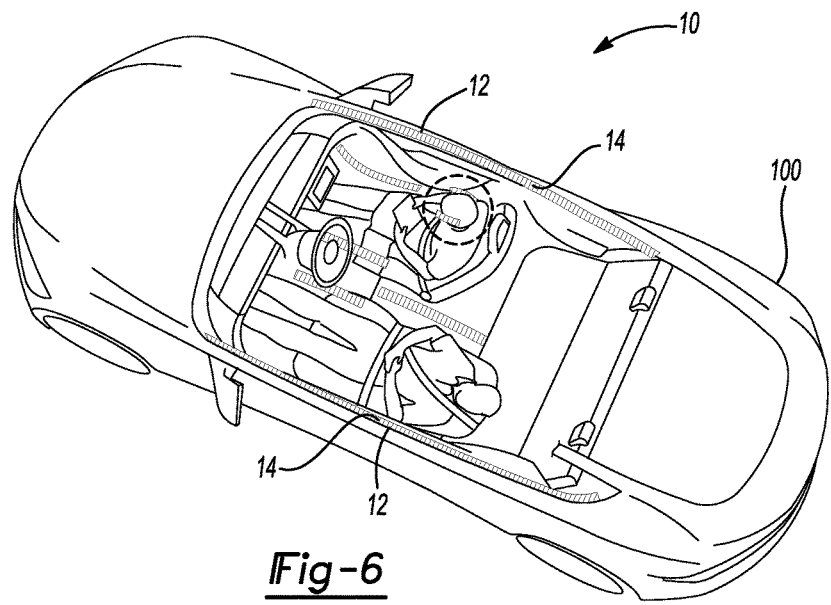
FIG. 6 illustrates the universal motion sickness countermeasure system of the present teachings being incorporated into the passenger compartment of a vehicle according to some embodiments.
Figure 7:
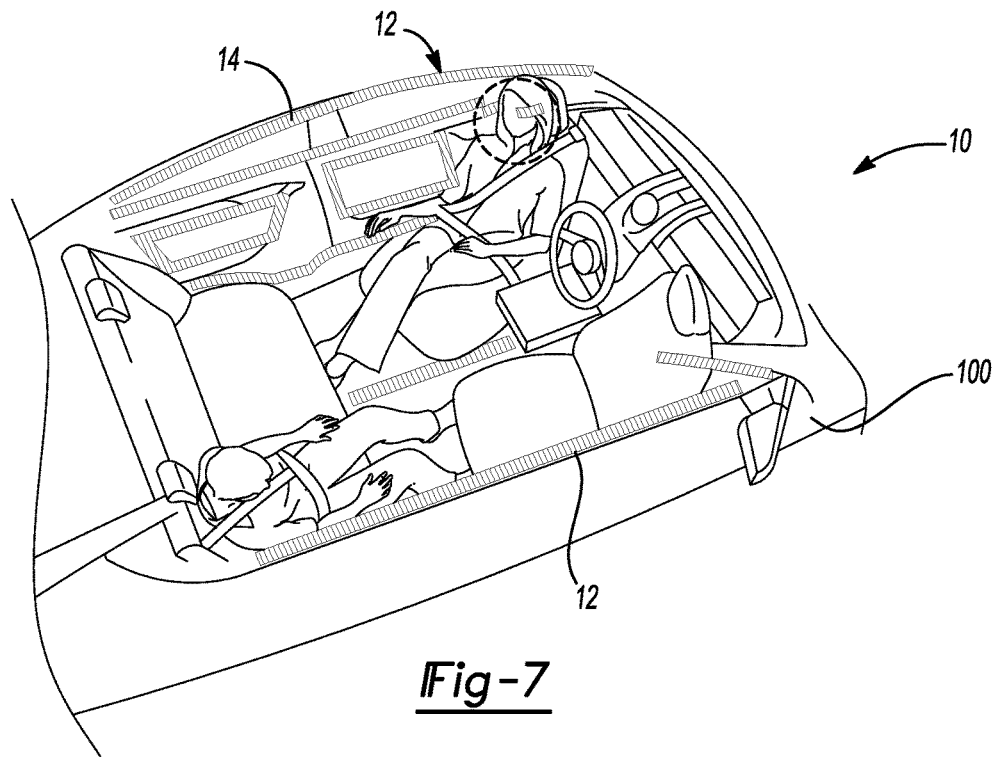
FIG. 7 illustrates the universal motion sickness countermeasure system of the present teachings being incorporated into the passenger compartment of a vehicle according to some embodiments.
Figure 8:
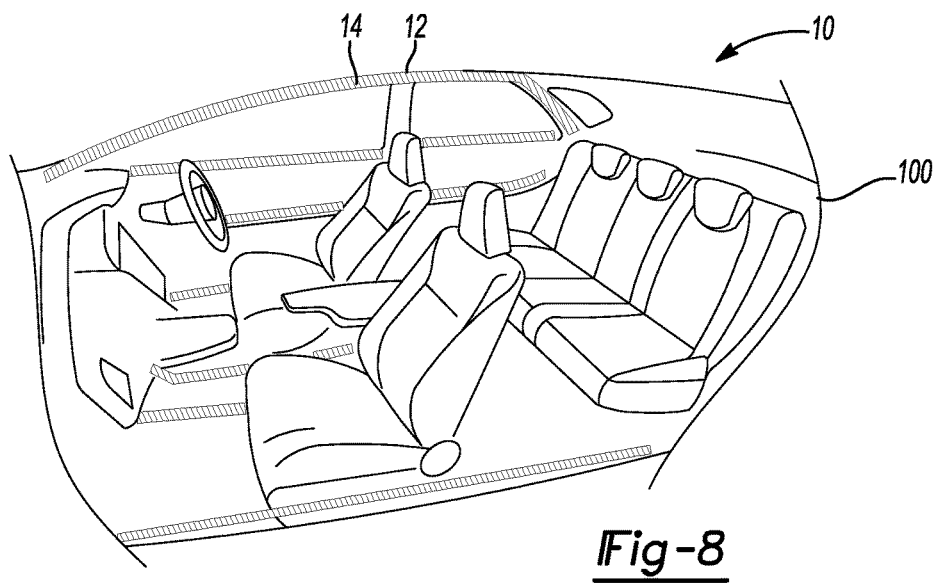
FIG. 8 illustrates the universal motion sickness countermeasure system of the present teachings being incorporated into the passenger compartment of a vehicle according to some embodiments.
Figure 9:
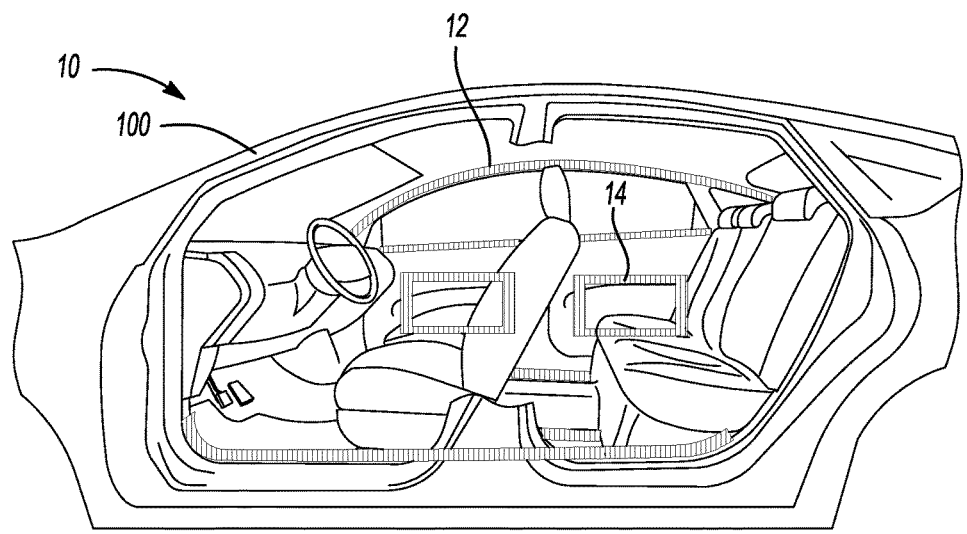
FIG. 9 illustrates the universal motion sickness countermeasure system of the present teachings being incorporated into the passenger compartment of a vehicle according to some embodiments.

As illustrated in FIGS. 2 and 4, universal motion sickness countermeasure system 10 can comprise a wearable array of lights or similar visual stimuli. To this end, universal motion sickness countermeasure system 10 can comprise a wearable frame member 200 having universal motion sickness countermeasure system 10 incorporated therein. Frame member 200 can be generally configured as conventional eyeglasses or goggles having peripheral output, namely light elements 14 and/or distal ends 26 of the plurality of light pipes 24. However, in some embodiments, universal motion sickness countermeasure system 10 can be incorporated into headwear, such as hat brims, ear mounts, or other wearable fixtures having light elements 14 and/or distal ends 26 of the plurality of light pipes 24. It should be understood that universal motion sickness countermeasure system 10 can comprise any wearable solution that enables at least peripheral access to a user's visual system. The current wearable embodiment can be installed in a variety of wearable items, and, importantly, requires only a small portion of the user's peripheral field of view to be obstructed by the device.

As illustrated in FIGS. 6-9, universal motion sickness countermeasure system 10 can comprise an array of lights or similar visual stimuli incorporated into the structure of the vehicle 100. To this end, universal motion sickness countermeasure system 10 can comprise light elements 14 and/or distal ends 26 of the plurality of light pipes 24 fixedly mounted or otherwise supported by any portion of vehicle 100, including, but not limited to, pillars, headliner, roof, sidewalls, doors, seats, floor, dashboard, console, windows or areas traditionally used as windows, and the like.

It should be understood that the output of universal motion sickness countermeasure system 10 can be tailored to the individual user and/or the orientation of the user, such that controller 16 activates the plurality of light elements 14 to produce a resultant light pattern that is likely to complement the vestibular system of the user. Therefore, sensors can be provided, either incorporated into either the wearable solution and/or the vehicle solution, that detect the orientation and/or positioning of the user to provide the proper resultant light pattern that would naturally be observed by the user in that orientation. That is, if the user is seated in a reclined position, the wearable solution can output resultant light pattern that matches the direction of travel irrespective of the orientation of the frame member 200.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A motion sickness countermeasure system for a user within a vehicle, the motion sickness countermeasure system comprising:
   a light array system configured to output visual stimuli presented only in a peripheral field of view of the user; and
   a controller outputting a control signal to the light array system configured to activate the light array system in such a way as to mimic the visual input one would receive if one were to look outside the vehicle.

2. The motion sickness countermeasure system according to claim 1 wherein the light array system comprises:
   a power source; and
   a plurality of light elements each discretely coupled to the controller for receiving the control signal and selectively activating in response thereto as a sequence of light activations of each of the plurality of light elements to create a perceived motion within the peripheral field of view of the user.

3. The motion sickness countermeasure system according to claim 2 further comprising:
   a plurality of light pipes individually coupled to each of the plurality of light elements, each of said plurality of light pipes transmitting light energy from each of the plurality of light elements to a distal end of the light pipe.

4. The motion sickness countermeasure system according to claim 3 wherein the distal end of the plurality of light pipes is arranged in an inclined surface relative to a visual perspective of the user.

5. The motion sickness countermeasure system according to claim 1 wherein the controller outputs the control signal to the light array system to activate the light array system to mimic velocity of the vehicle.

6. The motion sickness countermeasure system according to claim 1 wherein the light array system is mounted to the vehicle.

7. The motion sickness countermeasure system according to claim 6 wherein the light array system is mounted to at least one of an A-pillar, B-pillar, windshield, door, floor, forward panel, side panel, and seat of the vehicle.

8. The motion sickness countermeasure system according to claim 1 wherein the light array system is portable.

9. The motion sickness countermeasure system according to claim 1 wherein the light array system is wearable by an occupant.

10. The motion sickness countermeasure system according to claim 1 wherein the light array system is attached to an occupant.

11. The motion sickness countermeasure system according to claim 1 wherein the light array system comprises a headset worn by an occupant.

12. The motion sickness countermeasure system according to claim 1 wherein the light array system comprises glasses worn by an occupant.

13. A motion sickness countermeasure system for a user, the motion sickness countermeasure system comprising:
   a vehicle;
   a light array system configured to output visual stimuli presented in a peripheral field of view of the user; and
   a controller outputting a control signal to the light array system configured to activate the light array system in such a way as to mimic the visual input one would receive if one were to look outside the vehicle.

14. The motion sickness countermeasure system according to claim 13 wherein the light array system comprises:
   a power source; and
   a plurality of light elements each discretely coupled to the controller for receiving the control signal and selectively activating in response thereto as a sequence of light activations of each of the plurality of light elements to create a perceived motion within the peripheral field of view of the user.

15. The motion sickness countermeasure system according to claim 14 further comprising:
   a plurality of light pipes individually coupled to each of the plurality of light elements, each of said plurality of light pipes transmitting light energy from each of the plurality of light elements to a distal end of the light pipe.

16. The motion sickness countermeasure system according to claim 15 wherein the distal end of the plurality of light pipes is arranged in an inclined surface relative to a visual perspective of the user.

17. The motion sickness countermeasure system according to claim 13 wherein the controller outputs the control signal to the light array system to activate the light array system to mimic velocity of the vehicle.

18. The motion sickness countermeasure system according to claim 13 wherein the light array system is mounted to at least one of an a-pillar, b-pillar, windshield, door, floor, forward panel, side panel, and seat of the vehicle.

19. The motion sickness countermeasure system according to claim 13 wherein the vehicle is chosen from the group consisting of aircraft, ships, boats, and trains.

20. The motion sickness countermeasure system according to claim 13 wherein the light array system comprises at least one of LEDs, LCDs, and video displays.

* * * * *